United States Patent [19]

Shouda et al.

[11] 4,308,871
[45] Jan. 5, 1982

[54] CUFF MECHANISM FOR BLOOD PRESSURE MEASURING SYSTEM

[75] Inventors: Hiroyuki Shouda; Kenichi Sakurado, both of Komaki, Japan

[73] Assignee: Nippon Colin Co., Ltd., Aichi, Japan

[21] Appl. No.: 110,622

[22] Filed: Jan. 9, 1980

[30] Foreign Application Priority Data

Feb. 7, 1979 [JP] Japan .................................. 54-12978
Feb. 7, 1979 [JP] Japan .................................. 54-12979

[51] Int. Cl.³ .............................................. A61B 5/02
[52] U.S. Cl. .................................................. 128/686
[58] Field of Search .............................. 128/680-686, 128/75, 84-85

[56] References Cited

U.S. PATENT DOCUMENTS

3,888,243 6/1975 Powlan ................................ 128/75
3,935,984 2/1976 Lichowsky et al. ................ 128/686
4,206,765 6/1980 Huber .................................. 128/686

Primary Examiner—Robert W. Michell
Assistant Examiner—Francis J. Jaworski
Attorney, Agent, or Firm—Browdy and Neimark

[57] ABSTRACT

A cuff mechanism for use with a blood pressure measuring apparatus which comprises a flexible band, accommodating a cuff within the same wrappable (windable) in a cylindrical roll about an arm of a human body, and an air cylinder as a pulling means for pulling the band to tightly compress the band about the arm operated by pressurized air supplied in common with an air bag disposed in the band from an air supplying means. The flexible band is provided with, on occasion, a plurality of cross cuts formed on both sides thereof for better adaptation to the shape of an arm, and the air cylinder is sometimes pivoted to a stationary member swingably with a pin for being variable in the pulling direction of the band for better adaptation of the band to an arm of ununiform thickness and of irregular surface.

7 Claims, 15 Drawing Figures

CUFF MECHANISM FOR BLOOD PRESSURE MEASURING SYSTEM

FIELD OF THE INVENTION

This invention relates to a cuff mechanism for use with a blood pressure measuring apparatus and more particularly to a smoothly operative cuff mechanism, simplified in structure and excellent in safety which can be automatically wrapped about a portion of a person's body in measuring a person's blood pressure.

BACKGROUND OF THE INVENTION

Blood pressure measuring method, in the conventional way, comprises wrapping a cuff (or manchette) composed of an air-bag, etc. about a portion of a person's body (human body), for example, an arm or leg; temporarily interrupting or closing off blood circulation through an artery by contracting or compressing a portion of a person's body with the air pressure supplied to the cuff; gradually decreasing the air pressure in the cuff while detecting Korotkov's sounds (i.e. frictional sounds between the artery wall and the blood flow) by the use of a sound detector, etc.; and detecting the cuff pressure values at the time when the Korotkov's sounds are produced and begin to disappear for determining a maximal blood pressure (systolic) and a minimal blood pressure (diastolic).

In recent years, an automatic sphygmomanometer which detects Korotkov's sounds and indicates blood pressure by providing a sound collector having a microphone, etc. within the cuff thereof has been developed and widely used to make the blood pressure measurement speedy and easy. Further, such an automatic cuff mechanism as proposed in U.S. Pat. No. 3,935,984 has been developed as a cuff mechanism for the so-called automatic sphygmomanometer to permit mechanically and automatically wrapping a person's arm in a cuff. As a result, the use of the automatic sphygmomanometer has become remarkably easier.

However, the above-mentioned conventional automatic sphygmomanometer involves many problems to be solved. Since it wraps a person's arm or leg with a cuff which is attached to a flexible band, with one end of the band being fixed, and mechanically pulling the other end portion thereof by a combination of a motor, gear, etc., the pulling means is likely to be remarkably complicated in structure and tends to easily get out of order. There is an inherent problem of producing mechanical noise during its operation. Besides, it is still difficult to maintain a suitable pulling force, even if a torque motor is used. Further, there is a danger of presenting an excessive pulling when the pulling means gets out of order.

Moreover, another important or serious problem is that difficulty arises in making a cuff closely contact with the portion of a person's body when the thickness of the portion is not uniform, since the cuff is mechanically and automatically wrapped. In other words, although the portion subjected to a blood pressure measurement is an upper arm of a person as a rule, the thickness of the same is often non-uniform, for example, in case of a sportsman who has unusually developed muscles in that portion. Therefore, in the conventional automatic sphygmomanometer where the band is pulled and compressed almost in a perpendicular direction to the center line of the upper arm, the cuff does not necessarily contact with the upper arm closely and uniformly, thereby a vacant or uncontacted space being formed between the slender part of the upper arm and the cuff. This is the reason why errors appear in blood pressure measuring.

SUMMARY OF THE INVENTION

Thus, it is an object of the invention to provide a cuff mechanism of simple structure, safe and smoothly operative, by solving the above-mentioned many problems and skillfully utilizing pressurized air, especially the air supplied by an air supplying means which is included in the sphygmomanometer itself.

Another object of the invention is to provide a cuff mechanism which can be wrapped and held in a most suitable state about a portion of a person's body, especially an arm or leg, where the thickness is not uniform.

Other objects of the invention will become apparent to those skilled in the art from the following detailed description of the preferred embodiments when read in connection with the accompanying drawings.

An important feature of this invention resides in the provision of a cuff mechanism for use with a blood pressure measuring system, including a flexible band having one end fixed, being almost cylindrically wrapped or wound about a portion (hereinafter called an arm) of a person's body (hereinafter called a subject) accommodated, in which blood circulation is temporarily cut or closed off and firmly compressed about the portion (arm) received in the cylindrically rolled band by being pulled at the other end thereof, and a flexible air chamber disposed along a portion of the interior surface of the band between the flexible band and the arm of the subject such that further pressure can be exerted on that arm by supplying air into the flexible air chamber; wherein the other free end of the flexible band is secured to an air cylinder which pulls the band in a tangential direction to that cylindrical roll for circumferentially contracting the band about the arm of the subject. On the other hand, a sphygmomanometer generally includes an air supplying means which supplies air into a cuff (air-bag). Therefore it is very convenient to utilize this air supplied by the air supplying means to the air cylinder for thereby operating the same in order to pull the flexible band, which enables dispensing with another air supplying means for the air cylinder by doing away with an extra pressurized air producer and the driving source therefor. This will greatly contribute to the cost lowering of the cuff mechanism, not to mention miniaturization, lightening and simplification of the cuff mechanism.

Further, another important feature of this invention is the provision of a cuff mechanism for use with a blood pressure measuring system, wherein the pulling means, comprising an air cylinder to which the other free end of the flexible band is secured to pull the band in a tangential direction to the cylindrical roll for circumferentially contracting the band about the portion or the arm of the subject, is secured to a stationary member such that the direction toward which the flexible band is pulled can be varied according to the shape of the arm of the subject for allowing the air cylinder to pull the flexible band swinging along the lengthwise surface thereof in accordance with the shape of the arm of the subject. Therefore, the cuff can be compressed or contracted about the arm of the subject, even in case wherein the thickness of the arm is ununiform, with the band being uniformly closely contacted and rolled up (wound up) without forming a vacant or uncontacted space.

Still another important point of this invention is to provide a further devised flexible band of the above-mentioned structure. In other words, the flexible band is provided with a plurality of cross cuts arranged longitudinally with a predetermined interval on both sides of the portion thereof where it is wound about an arm of a subject. Therefore, the formation of a vacant space can be surely prevented, thereby resulting in an accurate blood pressure measurement, even if a cuff is wound about the arm of the subject whose thickness is not uniform. After all, the cross cuts arranged in the flexible band are to be forcibly opened in accordance with the thickness and shape of the arm of the subject to fit and adapt to the surface of the portion (arm) when the flexible band is wrapped and pulled for winding up even when the thickness of the arm is not uniform. Therefore, the cuff disposed inside the band comes to a closer contact than otherwise with the arm of the subject, forming no vacant space between them.

DETAILED DESCRIPTION OF THE PREFERRED EMBODIMENT

Figure 1:
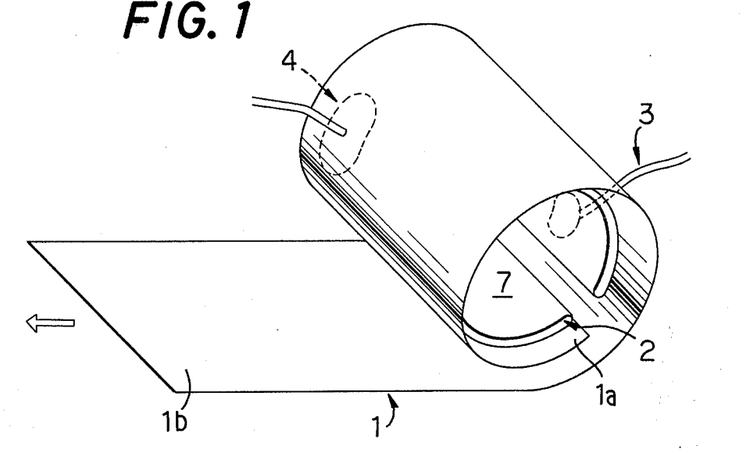
FIG. 1 is a schematic illustration showing a part of the winding portion in an ordinary automatic cuff mechanism.

Referring now to the drawing, FIG. 1 is a schematic illustration showing a part of the wrapping (winding) portion of a conventional automatic cuff mechanism. A flexible band 1 made of a metal strip or plastic sheet is almost cylindrically wrapped (rolled) for receiving a portion of a person's body (an arm) in which blood circulation is temporarily cut off, with one end 1a fixedly accommodated in a cylindrical enclosing member (not shown), and the other free end 1b pulled outwardly in a tangential direction marked with an arrow through a part of a circumferential wall of the cylindrical enclosure. And a cuff 2 of predetermined width constituting of a rubber air-bag is mounted along a portion of the interior surface of the flexible band 1 to form a flexible air chamber between the flexible band 1 and the arm of the subject. The cuff 2 is provided with an air supplying passage 3, through which air is sent under pressure thereinto, as a part of air supplying means, and a sound detector 4 having a microphone for detecting Korotkov's sounds in the artery.

The operation of the cuff mechanism is as follows: A patient or other subject person, whose blood pressure is to be measured, will insert a portion of his body, for example, an upper arm, into the cylindrical opening 7 (cylindrical roll) inside the flexible band 1. Then, the flexible band 1 will be pulled in the direction of the arrow to be wound about the upper arm inserted into the cylindrical opening 7, permitting the cuff 2 to come closely into contact with the upper arm. Thereafter, pressurized air will be sent through the air supplying passage 3 into the cuff 2 for applying further pressure to the upper arm, thereby temporarily closing off blood circulation in the artery there. Then, the air pressure in the cuff 2 will be gradually decreased while detecting Korotkov's sounds by the sound detector 4 placed in close contact with the upper arm, thereby detecting the production and extinction of the Korotkov's sounds for the measurement of a maximal blood pressure (systolic) and a minimal blood pressure (diastolic).

An example of such conventional automatic cuff mechanism is stated in detail in U.S. Pat. No. 3,935,984. The greater part of it shall be preferably referred to for understanding this invention.

Beside the foregoing structure and operation of the conventional automatic cuff mechanism this invention is featured in the provision of an air cylinder which carries out a series of actions in the automatic cuff mechanism with its air pressure.

Figure 2:
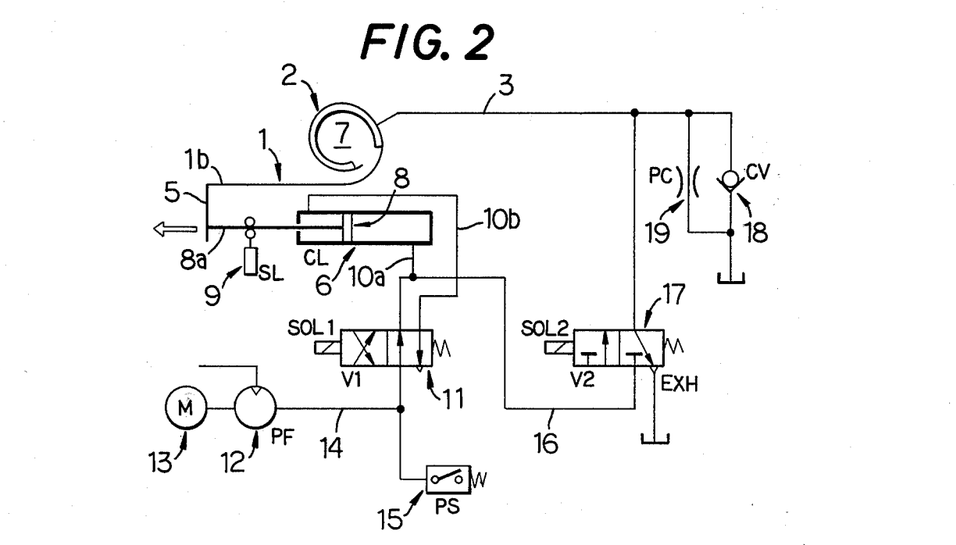
FIG. 2 is a circuit diagram showing various means and an air system in an embodiment of the mechanism of this invention.
Figure 3:
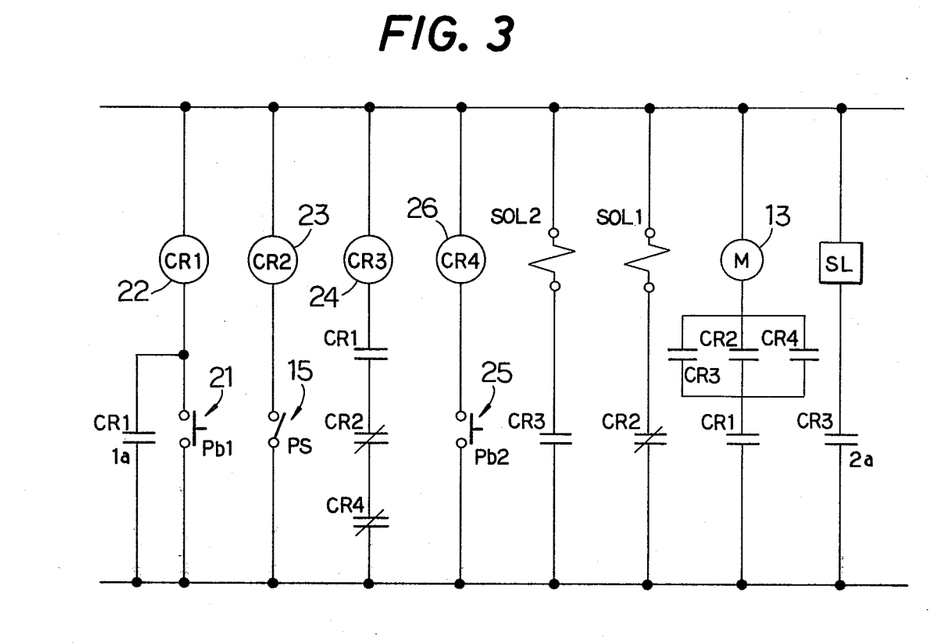
FIG. 3 is a view showing an electric circuit employed in the mechanism of FIG. 2.

FIG. 2 is a circuit diagram showing various means and an air system in an embodiment of the mechanism of this invention, and FIG. 3 is a view showing an electric circuit employed in the mechanism of FIG. 2.

As shown in FIG. 2, free end 1b of a flexible band 1 is secured through a connecting member 5 to the end portion of a piston rod 8a sliding in an air cylinder (CL) 6. Pressurized air flows into the air cylinder 6 to move a piston 8 for moving the piston rod 8a to the left (in the direction of an arrow). As a result, the flexible band 1 is pulled to the left (i.e. in a tangential direction to the cylindrically wrapped band 1) to be circumferentially contracted about the upper arm inserted. And the piston rod 8a is provided with a clamp (electromagnetic solenoid SL) 9, which clamps the leftwardly shifted piston rod 8a for preventing the same from moving either to the left and right. Therefore, the cylindrically wrapped flexible band 1 never returns to its original shape in spite of its elasticity. In other words, the piston rod 8a is provided with the clamp 9 to prevent the flexible band 1 from moving to the right, and thus not to loosen the tightening of the flexible band 1 wound about the upper arm inserted.

Communicating with the air cylinder 6 are passages 10a and 10b connected to a first valve means (four port solenoid operated valve V1, called the first solenoid operated valve hereafter) 11. Pressurized air for filling the left and right chambers of the piston 8 is passed into the chambers through the passages 10a and 10b. An inlet of the first solenoid operated valve 11 is connected through a passage 14 to an air pump (PF) 12 which is driven by the driving means such as a motor (M) 13 to send pressurized air into the first solenoid operated valve 11. Also, a pressure switch (PS) 15 is connected to the passage 14 to be operated by the pressurized air from the air pump 12.

A passage 16, branching the passage 10a through which the pressurized air from the first solenoid operated valve 11 is passed into the right chamber in the air cylinder 6 to move the piston rod 8a in the direction of the arrow, is connected to a second valve means (three ports solenoid operated valve V2, called the second solenoid operated valve hereafter) 17. Pressurized air from the second solenoid operated valve 17 is passed through an air supplying passage 3 into a cuff 2. Branched from the passage 3 is disposed exhausting means including a check valve (CV) 18 and a throttle valve (PC) 19 for releasing the pressurized air in the cuff 2 into the atmosphere.

The foregoing air system in an embodiment of the mechanism of this invention is automatically operated as follows by means of an electric circuit (i.e. sequence circuit) shown in FIG. 3.

Initially, a relay (CR1) 22 is actuated by depressing a starting switch (Pb1) 21 so that a relay contact (CR1-1a) feeds current to the relay (CR1) 22, keeping it so that a relay contact (CR1-1a) may be selfheld. Then, the pressure switch 15 becomes "ON," since the air pressures in each passage and the air cylinder 6 are all zero. Therefore, a relay (CR2) 23 is actuated to rotate the motor 13 which drives the air pump 12, thus the pressurized air is sent through the passage 14 to the first solenoid operated valve 11. Since the contact (CR1-1a) is "ON," the solenoid coil (SOL1) of the first solenoid operated valve 11 operates the first solenoid operated valve 11 to lead the pressurized air from the air pump 12 to the passages 16 and 10a. The pressurized air led to the branched passage 10a is passed into the right chamber in the air cylinder 6 to push the piston 8 and piston rod 8a in the direction of the arrow. Thus, the one end 1b of the flexible band 1, which is secured to the piston rod 8a, is pulled in the direction of the arrow to circumferentially contract the band 1 about an arm of a subject (an upper arm), permitting the cuff 2 disposed inside the band 1 to come closely into contact with the arm of the subject.

When the flexible band 1 begins to receive a proper pulling force to be snugly wrapped about the arm of the subject (i.e. when the piston 8 in the air cylinder 6 begins to receive a predetermined air pressure), the pressure switch 15 is operated to turn the relay (CR2) 23 "OFF." Incidentally, a relay (CR3) 24 is energized, and a contact (CR3-2a) feeds current to the electromagnetic solenoid (SL) to allow the clamp 9 to clamp the band 1 (actually at the piston rod 8a) so that the snugly wrapped flexible band 1 never returns to its original shape in spite of its elasticity. Also, the contact (CR3-2a) feeds current to the solenoid coil (SOL2) of the second solenoid operated valve 17 to operate the second solenoid operated valve 17 to lead the pressurized air from the passage 16 to the cuff 2 through the passage 3. Owing to the foregoing switching action of valve means, the pressurized air having a relatively high air pressure in the air cylinder 6 is rapidly led through the passages 10a, 16 and 3 to the cuff 2 by an accumulator-like action of the air cylinder 6; thus the air pressure in the cuff 2 is rapidly heightened, while the pressurized air from the air pump 12 will suffice the still possible pressure shortage in the cuff 2. Therefore, the pressure in the cuff 2 is rapidly heightened by the effective usage of the air in the air cylinder 6. It is of course desirable in the blood pressure measurement that the pressure in the cuff 2 should be rapidly heightened. After the air pressure in the cuff 2 has attained a predetermined pressure enough for contracting the arm of the subject by the cuff 2 (to cut off blood circulation through the artery), the pressure switch 15 is operated to stop passing pressurized air into the cuff 2. In other words, the pressure switch 15 is operated to stop the motor 13 and air pump 12. Also, the second solenoid operated valve 17 operates to cut off the connection of the passage 3 leading to the cuff 2 and the passage 16.

Then, the throttle valve 19 in the exhaust means receives a command from another electric system in a blood pressure measuring system to be operated to release the pressurized air in the cuff 2 little by little into the atmosphere for gradually diminishing the air pressure in the cuff 2. Thus, the production and extinction of the Korotkov's sounds in the blood vessel (blood circulation through which has been temporarily cut off by contracting the arm of the subject) is detected by the use of the sound detector 4 which is usually secured to the cuff 2, thereby the air pressure values at the time when the Korotkov's sounds are produced and ceased to exist are measured as a maximal blood pressure and a minimal blood pressure.

After the blood pressure measurement has been completed, a switch (Pb2) 25 is automatically operated to actuate a relay (CR4) 26. As a result, the second solenoid operated valve 17 becomes "OFF." The band 1 which has been clamped by the clamp (electromagnetic solenoid SL) 9 is set free. The cuff 2 is released from its contraction about the arm of the subject by releasing (exhausting) the pressurized air in the cuff 2 into the atmosphere. The first solenoid operated valve 11 leads the pressurized air from the air pump 12 driven by the motor 13 to the left chamber in the air cylinder 6 through the passage 10b to return the piston 8 and piston rod 8a to their original positions (to the right in FIG. 2), thereby the flexible band 1 is thoroughly released from the state of being pulled in the direction of the arrow for releasing in turn its contraction about the arm of the subject. Since the time required for the air pump 12 to be operated to return the piston 8 and piston rod 8a to their original positions is set, the motor 13, the air pump 12 and the air cylinder 6 are stopped due to a signal issued after the time has passed.

Figure 4:
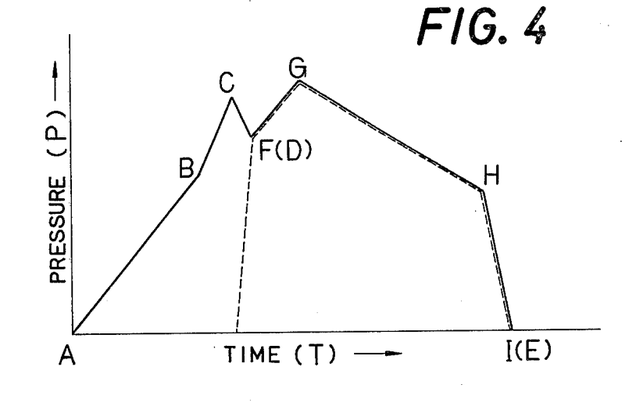
FIG. 4 is a graph which shows the varying of the air pressure in an air cylinder and a cuff in an embodiment of the mechanism of this invention.

A series of foregoing operations are further explained in detail from a viewpoint of the air pressure according to the graph shown in FIG. 4. In the figure, a solid line shows the air pressure (in the right chamber) in the air cylinder 6, and a broken line the air pressure in the cuff 2.

The point A shows the pressure before a blood pressure measurement begins. Depressing a starting switch 21 raises the pressure in the air cylinder 6, thereby the piston rod 8a is forced out from the air cylinder 6 to pull the flexible band 1 for circumferentially contracting it about a portion of a person's body (an upper arm) [the state of the point B]. Then, pressurized air is further supplied in the air cylinder 6 until the pressure switch 15 is operated (the state of the point C). After a predetermined suitable pressure has been reached, the electromagnetic solenoid (SL) is operated to clamp the flexible band 1, the first solenoid operated valve 11 and the second solenoid operated valve 17 are operated to lead the pressurized air in the air cylinder 6 to the cuff 2, and the air pressure in the cuff 2 is rapidly heightened by the accumulator-like action of the air cylinder 6 (the state of the point F). On the other hand, the pressure in the air cylinder 6 is lowered to the same level as in the cuff 2, since the pressurized air in the air cylinder 6 is led to the cuff 2 (the state of the point D). Then, pressurized air is further supplied into the cuff 2 to properly adjust the pressure in the cuff 2 (the state of the point G).

From the state of the point G, the air pressure in the cuff 2 is gradually decreased, thereby making Korotkov's sounds detection possible for the blood pressure measurement. After the blood pressure measurement has been completed, the pressure in the cuff 2 becomes the state of the point H. Then, the switch 25 receives a signal of measurement completion and becomes "ON," thereby releasing the pressurized air in the cuff 2 into the atmosphere and lowering the pressure in the cuff 2 down to the atmospheric pressure (the state of the point I). And the left chamber in the air cylinder 6 imparts pressure to the right chamber, and the piston rod 8a is consequently forced into the air cylinder 6 for returning the flexible band 1 to its original position (the state of the point E).

As mentioned above, the cuff mechanism of this invention differs in many points from conventional automatic cuff mechanisms where a flexible band is pulled by the combination of a motor, gear, etc. The structure of the cuff mechanism of this invention is notably simple, since a flexible band is pulled by an air cylinder which utilizes pressurized air. Disposition of two valve means also allows the cuff mechanism of this invention to operate smoothly. This invention thus provides a safe and meritorious automatic cuff mechanism, which is free from a trouble, because of its simple structure and capability of smooth operation. Moreover, mechanical noise is scarcely produced in the cuff mechanism of this invention, since an air cylinder carries out a series of actions in the cuff mechanism. Thus, the automatic cuff mechanism of this invention can be a very effective measurement apparatus for a patient whose mental stability is apt to be disturbed by noise. Since pressurized air is used all over and pressure measuring components included in the blood pressure measuring system can be simultaneously utilized for the control of the cuff mechanism of this invention, it is easy to present and keep a proper pulling force, if only pressure setting is obtained through an electrical circuit. Also, there is no danger of presenting an excessive pulling in this mechanism, since means (circuit) for preventing excess pressure usually used in a cuff can be effectively utilized for controlling the pulling force of the air cylinder in this invention.

In particular, the foregoing cuff mechanism embodying this invention utilizes the pressurized air in an air supplying means to a cuff, which is generally included in a blood pressure measuring apparatus, concurrently for driving a band-pulling mechanism, so no other extra driving source (pressurized air producing means) is required for pulling a flexible band. This will greatly contribute to the cost lowering of the cuff mechanism, not to mention miniaturization, lightening and simplification of the cuff mechanism. Moreover in the present invention, owing to the switching action of the valve means the pressurized air having a high pressure in an air cylinder is led to a cuff, and the air pressure in the cuff can be rapidly heightened. Therefore, the time required for the air supplying into the cuff can be reduced, which greatly contributes to the shortening of the time required for a blood pressure measurement. Further, leading of the pressurized air is not limited to either one air chamber but allowed to both chambers divided by the piston in an air cylinder, which promotes the piston to be restored to its original state by positively adding the air pressure on the original restoring force by the elasticity of the band itself. This facilitates the release of an arm of a subject from a cuff mechanism. This is also of great benefit to the shortening of the time required for a blood pressure measurement.

Clearly, this invention is not limited to the example described, and variations and modifications thereof may occur to those skilled in the art once they become familiar with the basic concepts of this invention within the true spirit and scope of this invention. For example, the air cylinder 6 can be disposed on the straight line drawn in the direction toward which the flexible band 1 is pulled, though the air cylinder 6 is disposed such that the piston rod 8a is pushed out almost parallel to the direction toward which the flexible band 1 is pulled by means of employing a connecting member 5 in the example described above. Further, the one end 1b of the flexible band 1 may be secured directly, or through any other suitable connecting member than the piston rod 8a, to the cylinder portion of the air cylinder 6. Moreover, various kinds of clamps can be employed: the clamp 9 may clamp the flexible band 1 itself instead of the piston rod 8a; the clamp 9 may also clamp or engage with the connecting member 5 which has been moved as far as a predetermined position for preventing further movements. Besides, various kinds of valves can be employed as a valve means which acts as a control means in the switching of pressurized air from an air cylinder to a cuff. The valve disposition in passages may be suitably determined according to the function of individual valves.

Further, another important feature of this invention can be observed in the provision of a flexible band which is automatically pulled in various directions in accordance with the shape and thickness of an arm of a subject.

Figures 5A, 5B, 5D:
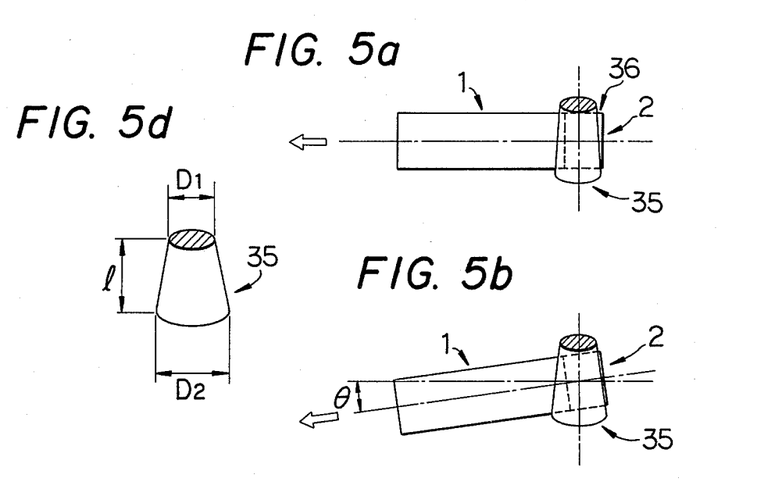
FIGS. 5(a)–(d) are schematic illustrations showing respectively a state in which a flexible band is wrapped about an arm of a subject in order to explain the principle of winding and pulling of the band in the mechanism of this invention.

In the above-mentioned automatic cuff mechanism, the flexible band is pulled almost in a perpendicular direction to the center line of its cylindrical portion (or a portion of a person's body inserted into the cylindrical portion). Therefore, a vacant space 36 is formed between an upper arm 35 and a cuff 2 when the flexible band 1 is pulled almost in an orthogonal direction to the center line of the upper arm 35 as shown in FIG. 5(a), unless the thickness of the upper arm is uniform. This provides many problems for a blood pressure measurement.

Figure 5C:
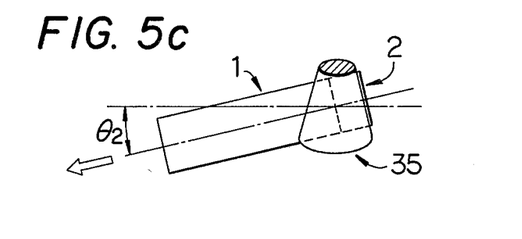

It will be understood that the cuff 2 comes to a close contact with the surface of the upper arm 35 if the flexible band 1 is pulled in an orthogonal direction to a slope of the upper arm 35 such that the flexible band 1 fits the slope of the upper arm 35 as shown in FIG. 5(b). In other words, the flexible band 1 must be pulled at an angle of $\theta$ to the pulling direction of FIG. 5(a). In the case of FIG. 5(c) where a large difference is recognized in the shape (thickness) between both end portions of a cone (an upper arm 35), the flexible band 1 must be pulled at a bigger angle ($\theta_2$) to the pulling direction of FIG. 5(a) to allow the flexible band 1 to fit the slope of the upper arm 35 more tightly.

In this way, the cuff 2 is allowed to be in close contact with a portion of a person's body (an upper arm 35), forming no vacant space 36 between them, if the flexible band 1 is pulled at an angle of $\theta$ which is determined by finding the degree of cone $[(D_2-D_1)/l]$ of a portion of a person's body (an upper arm 35) [see FIG. 5(d)].

Figure 6:
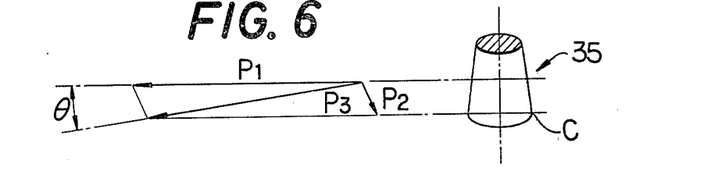
FIG. 6 is a schematic illustration to explain the moment applied to a flexible band.

As shown in FIG. 6, the moment applied to the flexible band 1 is swung or slipped off by the angle $\theta$ in the direction of $P_3$. In this instance $P_3$ denotes a resultant force obtained by combining the vector of $P_1$ and the vector of $P_2$, wherein $P_1$ is a force pulling the flexible band 1 in an orthogonal direction to the center line of the upper arm 35 and $P_2$ is a reaction force produced by the obstruction of the thickest end portion C of the cone at the time when the flexible band 1 is pulled.

Figure 7A:
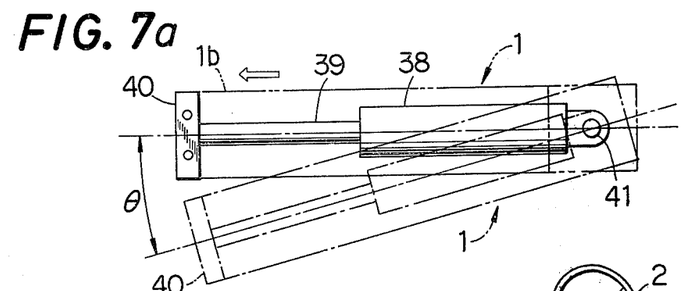
FIGS. 7(a) and (b) are a plan view and a schematic elevation of a pulling mechanism according to this invention.
Figure 7B:
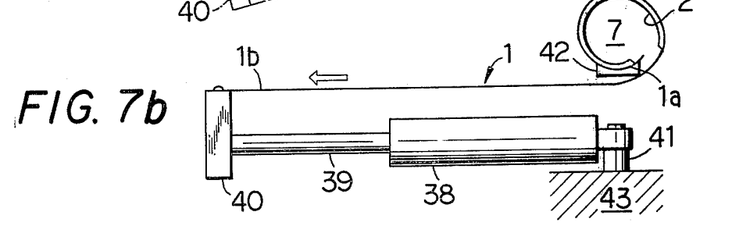

This invention attains the object by providing a very simple constitution based on the above-mentioned theory, and one embodiment of this invention is shown in FIGS. 7(a) and (b).

As illustrated in FIGS. 7(a) and (b), a flexible band 1 is cylindrically wrapped, with one end 1a secured to a stand 42 and the other end 1b extending tangentially from the lowest end of the cylinder secured to a connecting member 40, which is in turn secured to the end portion of a piston shaft 39 of an air cylinder 38. The other end portion of the piston shaft 39 of the air cylinder 38 is rotatably or swingably pivoted with a pin 41 beneath a cuff 2 to a stationary stand 43.

A patient or other subject person who wishes to have his blood pressure measured inserts a portion of his body first, for example, an upper arm, into the opening 7. Thereafter, air is supplied into the air cylinder 38 to move horizontally the piston shaft 39 of the air cylinder 38 for pulling the flexible band 1 in the direction of an arrow such that the pulling force circumferentially contracts the band 1 in a manner of gradually tightening the same about the upper arm, thus the cuff 2 mounted inside the band 1 comes into a close contact with the upper arm.

In FIG. 7(a), a solid line shows a state of the flexible band 1 pulled, in case of the upper arm being uniform in thickness. The piston shaft 39 of the air cylinder 38 moves in an orthogonal direction to the center line of the upper arm (cylinder). On the other hand, a two-dot-chain line shows a state of the flexible band 1 pulled, in case of the upper arm being ununiform in thickness. As elucidated in FIGS. 5 and 6, the force of the piston shaft 39 is swung by the angle $\theta$ in proportion to the degree of cone. The air cylinder 38 automatically shakes or swings its head by the angle $\theta$ about the pin (fulcrum) 41 to consequently pull the flexible band 1 in the shaked direction for tightening the flexible band 1 in winding about the upper arm, since the one end of the air cylinder 38 is rotatably pivoted to the pin 41. Therefore, the cuff 2 is made to come into 2 close contact with the upper arm of ununiform thickness, i.e., of cone shape forming no vacant space between the two.

The foregoing is one of the most preferred embodiments of this invention for a blood pressure measuring system which is required to be compact and simple. Another preferred embodiment of this invention is further shown in FIG. 8.

Figure 8:
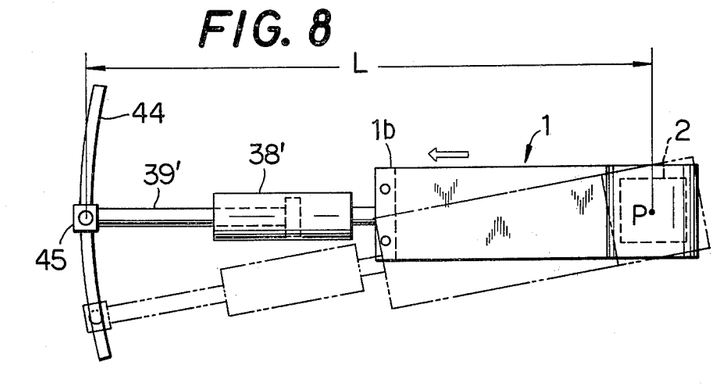
FIG. 8 is a schematic plan view of the mechanism of another embodiment of this invention.

The cuff mechanism shown in FIG. 8 differs from the cuff mechanism shown in FIG. 7 in constitution. In the latter case, one end of the air cylinder 38 near the cuff is rotatably secured to a stationary stand 43 and one end of the piston shaft 39 is secured through the connecting member 40 to the other end 1b of the flexible band 1, thus the flexible band 1 pulled parallel to the moving direction of the piston shaft 39. In the cuff mechanism shown in FIG. 8, an air cylinder 38' is disposed on the extension of the line drawn in the direction toward which a flexible band 1 is pulled, with one end of the air cylinder 38' secured to the other end 1b of the flexible band 1 and one end of a piston shaft 39' engaged through a sliding member 45 to an arcuate guide channel 44; thus the flexible band 1 is pulled by the contraction movement of the air cylinder 38'. The arcuate guide channel 44 is disposed on the circumference of a circle whose radius is L (i.e. the distance between the cylindrical portion center P of the flexible band 1 and the sliding member 45). The sliding member 45 is guided to move along the guide channel 44 in accordance with the thickness of the portion (arm) of a person's body inserted into the cylindrical portion of the flexible band 1, thus the direction toward which the flexible band 1 is pulled is automatically varied as stated above. In the figure, a solid line shows a state of the flexible band 1 pulled in a case where the arm of the subject being uniform in thickness. On the other hand, a two-dot-chain line shows a state of the flexible band 1 pulled, in a case where the arm of the subject being ununiform in thickness.

After all, this invention attempts to provide a pulling means (air cylinder 38, 38') which is rotatably or swingably connected to a stationary member (stand) so that the direction toward which the flexible band 1 is pulled can be varied in accordance with the shape (thickness) of an arm of a subject. Various kinds of fitting structures are acceptable, if they satisfy the requirement mentioned above.

Figure 9A:
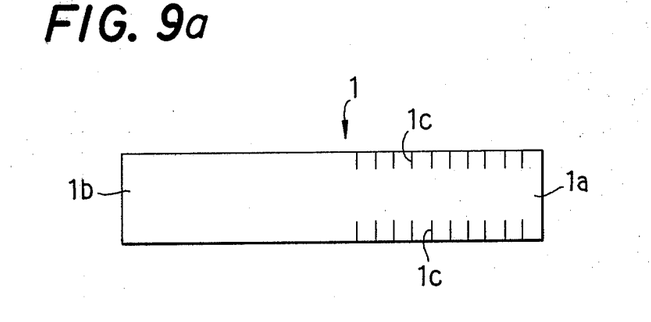
FIGS. 9(a), (b) and (c) are a plan view of a flexible band used in this invention, a view illustrating a state in which the flexible band is wrapped about an arm of a subject; and an enlarged detail view illustrating a state in which the flexible band is wrapped i.e., a perspective view from the direction of A in FIG. 9(b).
Figure 9B:
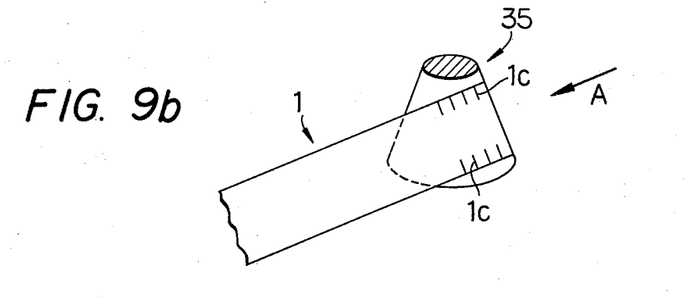
Figure 9C:
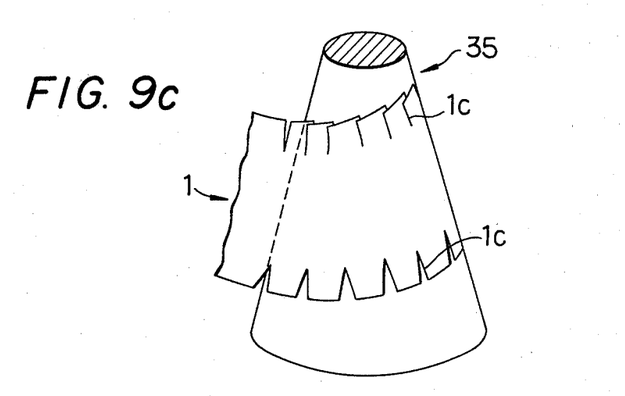

A further desirable feature of this invention is to provide a flexible band which is provided with a plurality of cuts as shown in FIG. 9, which makes the attainment of the object of this invention much far easier.

In FIG. 9(a), the flexible band 1 is provided with a plurality of cross cuts 1c arranged longitudinally with a predetermined interval from each other on both sides of the portion which is wound about an arm of a subject. As shown in FIGS. 9(b) and (c), the cuts 1c arranged in the flexible band 1 are to be opened split according to the thickness and roughness of an arm 35 of a subject to fit better the surface of the arm 35 when the flexible band 1 is pulled and wrapped about an arm of ununiform thickness and irregular surface. Therefore, the cuff 2 disposed inside the band 1 is able to come to a close contact with the arm of the subject like this, thus bringing about an accurate blood pressure measurement. Although the dimension and the interval of the cuts 1c are properly determined by the material of the flexible band 1, the pulling force exerted on the flexible band 1, etc., about 3–4 cm of cuts 1c are arranged with an interval of about 3 cm on both sides of the flexible band 1 as a rule, since the width of the flexible band 1 is ordinarily standardized at 14 cm.

This invention is not limited to a few examples described above, and variations and modifications thereof may occur to those skilled in the art once they become familiar with the basic concepts of this invention within the true spirit and scope of this invention.

What is claimed is:

1. A cuff mechanism for use with a blood pressure measuring system including a flexible band, with one end secured, being generally cylindrically rolled for receiving a portion of a person's body in which blood circulation is temporarily cut off and compressed about the portion received in the cylindrical roll by being pulled at the other end thereof, and a flexible air chamber lying along a portion of the interior surface of the band between the flexible band and said portion of said person's body such that further pressure can be exerted on said portion of said person's body by filling the flexible air chamber with air, wherein the other free end of said flexible band is connected to an air cylinder which pulls the band in a tangential direction to the cylindrical roll for circumferentially contracting the band about said portion of said person's body, said air cylinder being connected to an air supplying means which supplies air to said flexible air chamber and to said air cylinder, said mechanism further including controlling means for controlling the air supplied through said air supplying means to be led to either of said flexible air chamber and said air cylinder, and restraining means for preventing said flexible band which has been pulled by said air cylinder from moving in order to keep it in a state of being tightly pulled.

2. A cuff mechanism of claim 1, wherein air is led through two separate passages to said air cylinder for allowing the same to carry out mutually inverted operations, and said controlling means supplies air into said two separate passages.

3. A cuff mechanism of claim 1, wherein the switching action of said controlling means connects said air cylinder to said flexible air chamber so that the pressurized air passed into said air cylinder for pulling said flexible band is supplied into said flexible air chamber.

4. A cuff mechanism for use with a blood pressure measuring system including a flexible band, with one end secured, being substantially cylindrically rolled for receiving a portion of a person's body in which blood circulation is temporarily cut off and compressed about the portion received in the cylindrical roll by being pulled at the other end thereof, and a flexible air chamber lying along a portion of the interior surface of the band between the flexible band and said portion of said person's body such that further pressure can be exerted on said portion of said person's body by filling the flexible air chamber with air, wherein a pulling means, to which the other free end of said flexible band is secured to pull the band in a tangential direction to the cylindrical roll for circumferentially contracting the band about said portion of said person's body, comprises an air cylinder operated by the pressurized air led thereinto for pulling said flexible band secured to one end of said air cylinder by the expansion and contraction of said air cylinder, and direction means for controlling the angular direction in which said flexible band is pulled by said pulling means in response to variations in the shape of the portion of the person's body about which the band is wrapped, said direction means comprising securing means for securing said air cylinder to a stationary member such that the direction toward which the flexible band is pulled can be varied angularly with reference to an axis perpendicular to the cylindrical roll of said band and in accordance with the shape of said portion of said person's body for allowing the pulling means to pull said flexible band along the lengthwise surface of said flexible band.

5. A cuff mechanism of claim 4, wherein the free end portion of said flexible band is secured to one end of said air cylinder, and the other end of said air cylinder is rotatably secured to a stationary member, and said flexible band can be thereby pulled in varied direction due to the extension of said air cylinder.

6. A cuff mechanism of claim 4, wherein the flexible band includes means to accommodate for variations in circumference along the length of the portion of the person's body about which the flexible band is wrapped, said means comprising a plurality of cross cuts arranged in series along the length of said band at predetermined intervals from each other on both sides of a portion thereof which is wound about said portion of said person's body.

7. A cuff mechanism for use with a blood measuring system comprising a flexible band having a secured end and a movable end, said flexible band being substantially cylindrically rolled for receiving a patient's limb in which blood circulation is temporarily cut off by compression about the limb received in the cylindrical roll by pulling the free end of said flexible band, a flexible air chamber lying along a portion of the interior surface of said band between said flexible band and the patient's limb such that further pressure can be exerted on the patient's limb by filling the flexible air chamber with air, the free end of said flexible band being connected to an air cylinder for pulling the band in a tangential direction to the cylindrical roll for circumferentially contracting said cylindrical roll about the patient's limb, and air supply means for supplying air to both said flexible air chamber and said air cylinder, and including a plurality of valves and a pressure sensitive switch.

* * * * *